United States Patent
Thompson

(10) Patent No.: US 7,667,065 B2
(45) Date of Patent: Feb. 23, 2010

(54) HIGH NUCLEATION DENSITY ORGANOMETALLIC COMPOUNDS

(75) Inventor: David M. Thompson, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 556 days.

(21) Appl. No.: 11/497,351

(22) Filed: Aug. 2, 2006

(65) Prior Publication Data

US 2008/0032503 A1    Feb. 7, 2008

(51) Int. Cl.
*C07F 17/00*    (2006.01)
*C07F 15/00*    (2006.01)

(52) U.S. Cl. .................... 556/136; 534/15; 438/681; 427/248.1

(58) Field of Classification Search .............. 556/136; 438/681; 534/15; 427/248.1
See application file for complete search history.

(56) References Cited

U.S. PATENT DOCUMENTS 6,605,735 B2    8/2003    Kawano et al. ............ 556/136

OTHER PUBLICATIONS

Rein U. Kriss, Organimetallics, vol. 11, No. 2, pp. 497-499 (1992).*
Shibutami, T., et al. "Ruthenium Film with High Nuclear Density Deposited by MOCVD Using a Novel Liquid Precursor", *Electrochemcial and Solid-State Letters*, 6 (9) C117-C119 (2003).
Stahl, L. et al.. "Synthesis and Characterization of Bis(pentsdienyl) ruthenium Compounds", Organometallics 1983, 2, 1229-1234.
Stahl, L. et al. "Synthetic, Structural and PE Spectroscopic Studies on Bis(Pentadienyl) Compounds of Iron, Ruthenium and Osmium, The Role of the Heavy Metal", *Journal of Organometallic Chemistry*, 326 (1987) 257-268.
Hofer, O. et al. "Synthesis of Monosubstituted and Disubstituted Ruthenocenes" J. *Organometal. Chem.*, vol. 13. pp. 4443-4456 (1968).
Y. Matsui, et al. "Characteristics of Ruthenium Films Prepared by Chemical Vapor Deposition Using Bis (ethylcyclopentadienyl)ruthenium Precursor", *Electrochemical and Solid-State Letters*, 5 (1) C18-21 (2002).

* cited by examiner

*Primary Examiner*—Porfirio Nazario Gonzalez
(74) *Attorney, Agent, or Firm*—Iurie A. Schwartz

(57) ABSTRACT

This invention relates to high nucleation density organometallic ruthenium compounds. This invention also relates to a process for producing a high nucleation density organometallic ruthenium compound comprising reacting a bis(substituted-pentadienyl)ruthenium compound with a substituted cyclopentadiene compound under reaction conditions sufficient to produce said high nucleation density organometallic ruthenium compound. This invention further relates to a method for producing a film, coating or powder by decomposing a high nucleation density organometallic ruthenium compound precursor, thereby producing the film, coating or powder.

20 Claims, No Drawings

HIGH NUCLEATION DENSITY ORGANOMETALLIC COMPOUNDS

FIELD OF THE INVENTION

This invention relates to high nucleation density organometallic ruthenium compounds, a process for producing the high nucleation density organometallic ruthenium compounds, and a method for producing a film or coating therefrom.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate.

Preferably, chemical vapor deposition precursors are volatile, heat decomposable and capable of producing uniform films under chemical vapor deposition conditions. In producing thin films by chemical vapor deposition processes, precursors that are liquid at room temperature, rather than solids, often are preferred.

The semiconductor industry is currently considering the use of thin films of ruthenium metal for a variety of applications. Many organometallic complexes have been evaluated as potential precursors for the formation of these thin films. These include, for example, carbonyl complexes such as $Ru_3(CO)_{12}$, diene complexes such as $Ru(\eta^3-C_6H_8)(CO)_3$, $Ru(\eta^3-C_6H_8)(\eta^6-C_6H_6)$, beta-diketonates such as $Ru(DPM)_3$, $Ru(OD)_3$ and ruthenocenes such as $RuCp_2$, $Ru(EtCp)_2$.

Both the carbonyl and diene complexes tend to exhibit low thermal stabilities which complicates their processing. While the beta-diketonates are thermally stable at moderate temperatures, their low vapor pressures married with their solid state at room temperature make it difficult to achieve high growth rates during film deposition.

Ruthenocenes have received considerable attention as precursors for Ru thin film deposition. While ruthenocene is a solid, the functionalization of the two cyclopentadienyl ligands with ethyl substituents yields a liquid precursor that shares the chemical characteristics of the parent ruthenocene. Unfortunately, depositions with this precursor have generally exhibited long incubation times and poor nucleation densities.

U.S. Pat. No. 6,605,735 B2 discloses half-sandwich organometallic ruthenium compounds that have a cyclopentadienyl and pentadienyl group bonded to ruthenium. The cyclopentadienyl group can be mono-substituted or unsubstituted. The pentadienyl group can be mono-, di- or tri-substituted or unsubstituted. Certain substitution patterns are specifically excluded. It is stated in the patent that the inventors conducted extensive studies and found that the decomposition temperature of a ruthenocene can be lowered by substituting one of the cyclopentadienyl rings by linear pentadienyl. By introducing a single lower alkyl group into the cyclopentadienyl ring, it is stated in the patent that the half-sandwich organometallic ruthenium compounds have been found to be liquid at room temperature and exhibit favorable vaporization and decomposition properties. These compounds are used for producing a ruthenium-containing thin film by chemical vapor deposition.

In developing methods for forming thin films by chemical vapor deposition methods, a need continues to exist for chemical vapor deposition precursors that preferably are liquid at room temperature, have relatively high vapor pressure and can form uniform films. Therefore, a need continues to exist for developing new compounds and for exploring their potential as chemical vapor deposition precursors for film depositions. It would therefore be desirable in the art to provide a chemical vapor deposition precursor having a high nucleation density and producable with high yields.

SUMMARY OF THE INVENTION

This invention relates in part to high nucleation density organometallic ruthenium compounds. This invention also relates in part to a process for producing a high nucleation density organometallic ruthenium compound comprising reacting a bis(substituted-pentadienyl)ruthenium compound with a substituted cyclopentadiene compound under reaction conditions sufficient to produce said high nucleation density organometallic ruthenium compound. This invention further relates in part to a method for producing a film, coating or powder by decomposing a high nucleation density organometallic ruthenium compound precursor, thereby producing the film, coating or powder. High nucleation densities can be achieved by thermal decomposition of the precursor, which may lead to crystal growth initiation at many sites followed by propagation. The high nucleation density is of benefit since it leads to smoother films and shorter incubation times during deposition.

This invention relates in part to a high nucleation density organometallic ruthenium compound represented by the following formula:

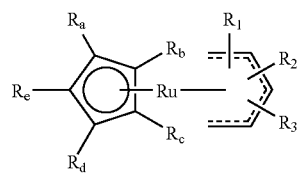

wherein $R_a$ and $R_c$ are the same or different and each represents a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, and $R_b$, $R_d$, $R_e$, $R_1$, $R_2$, and $R_3$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms.

This invention also relates to a process for producing high nucleation density organometallic ruthenium compounds which comprises reacting a bis(substituted-pentadienyl)ruthenium compound represented by the formula

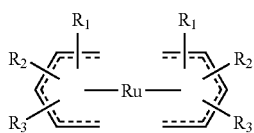

with a substituted cyclopentadiene compound represented by the formula

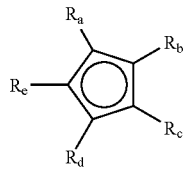

wherein $R_a$ and $R_c$ are the same or different and each represents a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, and $R_b$, $R_d$, $R_e$, $R_1$, $R_2$, and $R_3$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, under reaction conditions sufficient to produce said high nucleation density organometallic ruthenium compounds.

One method of increasing the nucleation density is to decrease the thermal stability of a precursor. Thermal decomposition of the precursor on the substrate provides a nucleation site around which further deposition can occur. Nucleation is the event that initiates crystal growth. It is preferable to have a high nucleation density since this leads to an increase in the numbers of crystals growing per unit area of substrate. This can result in coalescence of the film at decreased thicknesses. Higher nucleation can lead to thinner films. Properties of non-coalesced films are drastically different from those of coalesced films and are not suitable for semiconductor applications. Decreasing the minimum thickness of films for these semiconductor applications can provide device performance and cost advantages.

It has been found that the presence of two activating substituents on the cyclopentadienyl ring group, for example, a 1,3-substitution pattern (e.g., 1,3-dimethylcyclopentadienyl), versus the single substituent on the cyclopentadienyl ring group disclosed in U.S. Pat. No. 6,605,735 B2, e.g., 1-ethylcyclopentadienyl, provides increased electron density on the ring system. Increased electron density at the metal center results in a complex that is less thermally stable under typical deposition conditions.

Since openness of the metal center may be important to the nucleation process, it is important to recognize that the single ethyl substituent on the cyclopentadienyl ring group disclosed in U.S. Pat. No. 6,605,735 B2 may orient itself in a fashion to restrict access to the metal center and potentially even be loosely bound there via an agostic hydrogen interaction. Two methyl substituents on the cyclopentadienyl ring group in a specific 1,3-substitution pattern according to this invention will always remain planar with respect to the rest of the cyclopentadienyl group and should interfere less with the sterics of nucleation considering metal-substrate interaction is responsible for the increased nucleation density.

The invention has several advantages. For example, the method of the invention is useful in generating organometallic ruthenium compound precursors that have varied chemical structures and physical properties. Films generated from the high nucleation density organometallic ruthenium compound precursors can be deposited with a short incubation time, and the films deposited from the organometallic ruthenium compound precursors exhibit good smoothness.

Without wishing to be bound to any particular theory, there are two possible explanations for this behavior. The first is that the organometallic ruthenium compound precursors are thermally unstable at the wafer temperature and the precursor decomposes thermally. The second is that breaking open the cyclopentadienyl ring opens up better steric access to the metal center and permits better metal-substrate interactions.

A preferred embodiment of this invention is that the organometallic ruthenium compound precursors may be liquid at room temperature. In some situations, liquids may be preferred over solids from an ease of semiconductor process integration perspective.

This invention further relates to a process for producing high nucleation organometallic compounds which comprises reacting a metal salt ($M''X_n$) compound, a cyclopentadienyl compound (Cp) and a ligand (L'') under reaction conditions sufficient to form an intermediate compound; and reacting the intermediate compound with a pentadienide compound (PD) under reaction conditions sufficient to produce the high nucleation organometallic compounds, wherein M'' is a Group VIII metal, L'' is an electron pair donor compound, Cp is a disubstituted or polysubstituted cyclopentadienyl compound, and PD is a pentadienide-like salt.

This invention yet further relates to a process for producing high nucleation organometallic compounds which comprises reacting a metal salt ($M''X_n$) compound, a pentadienyl compound (PD') and a ligand (L'') under reaction conditions sufficient to form an intermediate compound; and reacting the intermediate compound with a cyclopentadienide compound (Cp') under reaction conditions sufficient to produce the high nucleation organometallic compounds, wherein M'' is a Group VIII metal, L'' is an electron pair donor compound, PD' is a pentadienyl compound, and Cp' is a disubstituted or polysubstituted cyclopentadienide-like salt.

This invention also relates in part to a method for producing a film, coating or powder. The method includes the step of decomposing at least one high nucleation density organometallic ruthenium compound precursor, and thereby producing the film, coating or powder.

DETAILED DESCRIPTION OF THE INVENTION

As indicated above, this invention relates in part to a high nucleation density organometallic ruthenium compound represented by the following formula:

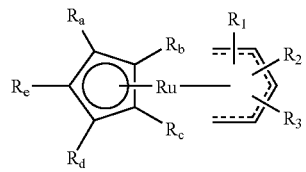

wherein $R_a$ and $R_c$ are the same or different and each represents a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, and $R_b$, $R_d$, $R_e$, $R_1$, $R_2$, and $R_3$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms.

Preferred high nucleation density organometallic ruthenium compounds are represented by the following formulae:

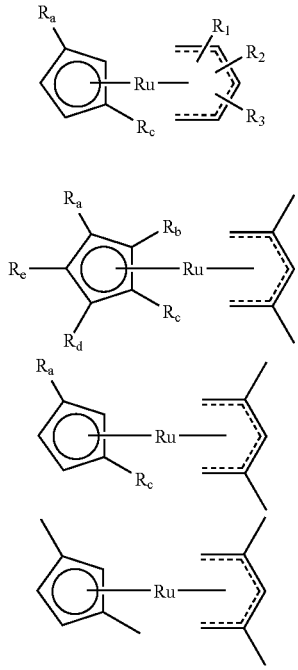

wherein $R_a$, $R_b$, $R_c$, $R_d$, $R_e$, $R_1$, $R_2$, and $R_3$ are as defined above. A more preferred high nucleation density organometallic ruthenium compound is depicted by the last formula above, i.e., (1,3-dimethylcyclopentadienyl)(2,4-dimethylpentadienyl)ruthenium.

Other high nucleation density organometallic compounds within the scope of this invention can be represented by the formula LML', preferably LRuL', where M is a transition metal, L is a substituted cyclopentadienyl group that may be selected from di-, tri-, tetra-, pentasubstituted cyclopentadienyl, indenyl, cyclic and acyclic allyls, and L' is a substituted or unsubstituted pentadienyl group. More preferably, L is selected from 1,3-substituted cyclopentadienyl and 1,3-substituted cyclopentadienyl-like groups, and L' is selected from substituted or unsubstituted pentadienyl groups and substituted or unsubstituted pentadienyl-like groups. Examples of 1,3-substituted cyclopentadienyl-like moieties include cycloolefin e.g., cyclohexadienyl, cycloheptadienyl, cyclooctadienyl rings, heterocyclic rings, aromatic rings, such as substituted benzenyl, and others, as known in the art. Examples of substituted or unsubstituted pentadienyl-like groups include linear olefinic groups, e.g., hexadienyl, heptadienyl, octadienyl, and others, as known in the art. Synthesis of these other high nucleation density organometallic compounds may be carried out by conventional methods such as described in U.S. Pat. No. 6,605,735 B2 or by methods described herein.

Still other high nucleation density organometallic compounds within the scope of this invention can be represented by the formula $(L)_2M'L'$ or $LM'(L')_2$, where M' is a lanthanide, L is the same or different and is a substituted cyclopentadienyl group that may be selected from di-, tri-, tetra-, pentasubstituted cyclopentadienyl, indenyl, cyclic and acyclic allyls, and L' is the same or different and is a substituted or unsubstituted pentadienyl group. More preferably, L is selected from 1,3-substituted cyclopentadienyl and 1,3-substituted cyclopentadienyl-like groups, and L' is selected from substituted or unsubstituted pentadienyl groups and substituted or unsubstituted pentadienyl-like groups. Examples of 1,3-substituted cyclopentadienyl-like moieties include cycloolefin e.g., cyclohexadienyl, cycloheptadienyl, cyclooctadienyl rings, heterocyclic rings, aromatic rings, such as substituted benzenyl, and others, as known in the art. Examples of substituted or unsubstituted pentadienyl-like groups include linear olefinic groups, e.g., hexadienyl, heptadienyl, octadienyl, and others, as known in the art. Synthesis of these other high nucleation density organometallic compounds may be carried out by conventional methods such as described in U.S. Pat. No. 6,605,735 B2 or by methods described herein.

Permissible substituents of the substituted cyclopentadienyl and cyclopentadienyl-like groups (L) and also the substituted pentadienyl and pentadienyl-like groups (L') include halogen atoms, acyl groups having from 1 to about 12 carbon atoms, alkoxy groups having from 1 to about 12 carbon atoms, alkoxycarbonyl groups having from 1 to about 12 carbon atoms or alkyl groups having from 1 to about 12 carbon atoms. Illustrative examples of these substituents are described above.

As indicated above, this invention encompasses other high nucleation density organometallic chemical vapor deposition precursors having two activating substituents on the cyclopentadienyl ring group in a specific 1,3-substitution pattern. Illustrative of such other organometallic compounds include, for example, $(Me_2Cp)PtMe_2$, $(Me_2Cp)Ir(COD=cyclooctadiene)$, $(Me_2Cp)Ir(C_6H_8=cyclohexadiene)$ and the like. Other metals which may be useful in the organometallic compounds of this invention include the transition metals and the lanthanides. Synthesis of these other high nucleation density organometallic compounds may be carried out by conventional methods such as described in U.S. Pat. No. 6,605,735 B2 or by methods described herein.

In U.S. Pat. No. 6,605,735 B2, the ethyl substituent on (1-ethylcyclopentadienyl)(2,4-dimethylpentadienyl)Ru may adopt conformations that restrict access to the metal center. Methyl substituents in a 1,3-substitution pattern on the cyclopentadienyl ring on the other hand result in a significantly decreased steric restriction to the metal center. If the method of nucleation involves a direct metal-substrate interaction, the (1,3-dimethylcyclopentadienyl)(2,4-dimethylpentadienyl) Ru of this invention may exhibit improved nucleation density over (1-ethylcyclopentadienyl)(2,4-dimethylpentadienyl) Ru.

The 1H NMR of (1-ethylcyclopentadienyl)(2,4-dimethylpentadienyl)Ru reveals cyclopentadienyl proton resonances that occur at 4.6 and 4.52 parts per million respectively. In comparison, the 1H NMR of (1,3-dimethylcyclopentadienyl)(2,4-dimethylpentadienyl)Ru reveals cyclopentadienyl proton resonances that occur at 4.34 and 4.23 parts per million. This implies that the cyclopentadienyl protons of (1,3-dimethylcyclopentadienyl)(2,4-dimethylpentadienyl)Ru are more shielded than the cyclopentadienyl protons of (1-ethylcyclopentadienyl)(2,4-dimethylpentadienyl)Ru. The increased electron density on the ring is believed to be due to the disubstitution pattern on the cyclopentadienyl ring of activating substituents. Based on the increased electron density on the cyclopentadienyl ring, the thermal stability of the organometallic ruthenium compounds is decreased resulting in an increase in nucleation density. Thinner films result from higher nucleation densities.

In general, many cyclopentadienyl based organometallic compounds have a tendency towards the solid state at room temperature. It has been found that the functionalization of the cyclopentadienyl ring with a 1,3-substitution pattern reduces the melting point of the species which is highly preferred by the end user.

It is highly uncertain and no way to accurately predict whether ruthenocenes will be liquids or solids. Ruthenocene, 1-methylruthenocene, and 1,1'-dimethylruthenocene are solids at room temperature. 1-ethylruthenocene, 1-ethyl-1'-methylruthenocene and 1,1'-diethylruthenocene are all liquids at room temperature. It is most interesting that when 2 methyl substituents are located on the same ring, a liquid or a solid may be obtained. 1,3-dimethylruthenocene is a liquid at room temperature, while 1,2-dimethylruthenocene is a solid (Hofer, O., et. al. *J. Organomet. Chem*, 1968, 13, 443).

As also indicated above, this invention relates to a process for producing high nucleation density organometallic ruthenium compounds which comprises reacting a bis(substituted-pentadienyl)ruthenium compound represented by the formula

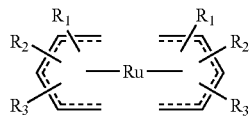

with a substituted cyclopentadiene compound represented by the formula

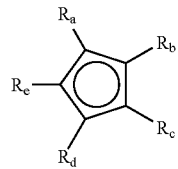

wherein $R_a$ and $R_c$ are the same or different and each represents a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, and $R_b$, $R_d$, $R_e$, $R_1$, $R_2$, and $R_3$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, under reaction conditions sufficient to produce said organometallic ruthenium compound.

A preferred bis(substituted-pentadienyl)ruthenium compound useful in the process of this invention can be represented by the formula

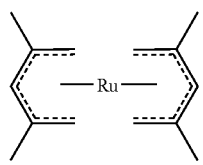

Illustrative substituted pentadiene compounds that can be reacted with the ruthenium starting materials described below include those represented by the formulae

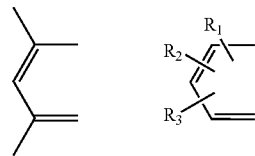

wherein $R_1$, $R_2$, and $R_3$ are as defined above.

Illustrative cyclopentadiene and cyclopentadienyl compounds that can be used in the processes of this invention include those represented by the formulae

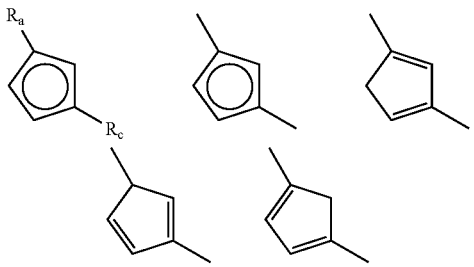

wherein $R_a$ and $R_c$ are as defined above.

Illustrative halogen atoms that may be used in $R_a$, $R_b$, $R_c$, $R_d$, $R_e$, $R_1$, $R_2$, and $R_3$ include, for example, fluorine, chlorine, bromine and iodine. Preferred halogen atoms include chlorine and fluorine.

Illustrative acyl groups that may be used in $R_a$, $R_b$, $R_c$, $R_d$, $R_e$, $R_1$, $R_2$, and $R_3$ include, for example, formyl, acetyl, propionyl, butyryl, isobutyryl, valeryl, 1-methylpropylcarbonyl, isovaleryl, pentylcarbonyl, 1-methylbutylcarbonyl, 2-methylbutylcarbonyl, 3-methylbutylcarbonyl, 1-ethylpropylcarbonyl, 2-ethylpropylcarbonyl, and the like. Preferred acyl groups include formyl, acetyl and propionyl.

Illustrative alkoxy groups that may be used in $R_a$, $R_b$, $R_c$, $R_d$, $R_e$, $R_1$, $R_2$, and $R_3$ include, for example, methoxy, ethoxy, n-propoxy, isopropoxy, n-butoxy, isobutoxy, sec-butoxy, tert-butoxy, pentyloxy, 1-methylbutyloxy, 2-methylbutyloxy, 3-methylbutyloxy, 1,2-dimethylpropyloxy, hexyloxy, 1-methylpentyloxy, 1-ethylpropyloxy, 2-methylpentyloxy, 3-methylpentyloxy, 4-methylpentyloxy, 1,2-dimethylbutyloxy, 1,3-dimethylbutyloxy, 2,3-dimethylbutyloxy, 1,1-dimethylbutyloxy, 2,2-dimethylbutyloxy, 3,3-dimethylbutyloxy, and the like. Preferred alkoxy groups include methoxy, ethoxy and propoxy.

Illustrative alkoxycarbonyl groups that may be used in $R_a$, $R_b$, $R_c$, $R_d$, $R_e$, $R_1$, $R_2$, and $R_3$ include, for example, methoxycarbonyl, ethoxycarbonyl, propoxycarbonyl, isopropoxycarbonyl, cyclopropoxycarbonyl, butoxycarbonyl, isobutoxycarbonyl, sec-butoxycarbonyl, tert-butoxycarbonyl, and the like. Preferred alkoxycarbonyl groups include methoxycarbonyl, ethoxycarbonyl, propoxycarbonyl, isopropoxycarbonyl and cyclopropoxycarbonyl.

Illustrative alkyl groups that may be used in $R_a$, $R_b$, $R_c$, $R_d$, $R_e$, $R_1$, $R_2$, and $R_3$ include, for example, methyl, ethyl, n-propyl, isopropyl, n-butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, and the like. Preferred alkyl groups include methyl, ethyl, n-propyl, isopropyl and cyclopropyl.

The process of the invention is useful in generating organometallic ruthenium compound precursors that have varied chemical structures and physical properties including high nucleation densities. A wide variety of reaction materials may be employed in the processes of this invention. For example, in the preparation of the bis(substituted-pentadienyl)ruthenium compounds, other ruthenium starting materials may be used in lieu of commercial grade Ru(III) chloride hydrate as in Example 1 below. Illustrative ruthenium materials include, but are not limited to, α-ruthenium(III)chloride, β-ruthenium(III)chloride, ruthenium(III)nitrate, $(PPh_3)_xRuCl_2$ (x=3–4) and the like. Alternative ruthenium starting materials may be added as solid solvates, solids, or solutions in lieu of the methanolic solution as in Example 1.

Also, in the preparation of the bis(substituted-pentadienyl) ruthenium compounds, other pentadienyl starting materials may be used in lieu of 2,4-dimethyl-1,3-pentadiene. Illustrative pentadienyl starting materials include, but are not limited to, 2,3-dimethyl-1,3-pentadiene, 3,4-dimethyl-1,3-pentadiene, 2,3,4-trimethyl-1,3-pentadiene, and the like.

The concentration of the ruthenium starting materials can vary over a wide range, and need only be that minimum amount necessary to react with the pentadienyl starting materials to give the bis(substituted-pentadienyl)ruthenium compounds used in the processes of this invention. In general, depending on the size of the reaction mixture, ruthenium starting material concentrations in the range of from about 1 millimole or less to about 1000 millimoles or greater, should be sufficient for most processes.

The concentration of the pentadienyl starting materials can vary over a wide range, and need only be that minimum amount necessary to react with the ruthenium starting materials to give the bis(substituted-pentadienyl)ruthenium compounds used in the processes of this invention. In general, depending on the size of the reaction mixture, pentadienyl starting material concentrations in the range of from about 1 millimole or less to about 1000 millimoles or greater, should be sufficient for most processes.

Other solvents may be used in place of methanol as in Example 1. Solvents containing alcohols such as ethanol, propanol, isopropanol, n-butanol, isobutanol, sec-butanol, tert-butanol and n-pentanol are preferred. Ethers and cyclic ethers (e.g. THF) are also suitable solvents. The choice of alcohol is not limited so long as it exists as a liquid at room temperature (25° C.).

Alkane solvents may be used in place of hexane for target product extraction. Odd carbon numbered alkane solvents (e.g. pentane/heptane/nonane), and cyclic alkanes are preferred over hexane since they pose less of a health hazard than even numbered alkanes (hexane/octane).

Other reducing agents may be used in the place of Zn as in Example 1. Illustrative of other reducing agents include, but are not limited to, Mg and Al.

The process of making bis(substituted-pentadienyl)ruthenium compounds can be operated over a wide range of process parameters and conditions. Reaction conditions such as temperature, pressure and contact time may also vary greatly and any suitable combination of such conditions may be employed herein. The reaction temperature may be the reflux temperature of any of the aforementioned solvents, and more preferably between about −40° C. to about 100° C., and most preferably between about −20° C. to about 80° C. Normally the reaction is carried out under ambient pressure and the contact time may vary from a matter of seconds or minutes to a few hours or greater. The reactants can be added to the reaction mixture or combined in any order. The molar ratio of Zn:Ru in the starting materials may vary from about 1.5 to about 100.

The cyclopentadiene compounds used in the processes of this invention can be prepared by conventional methods known in the art. For example, 1,3-dimethylcyclopentadiene can be readily synthesized in a one step process via a ring closing condensation of 5-methyl-5-hexen-2-one ($H_2C=C(CH_3)CH_2CH_2COCH_3$) procurable from Aldrich and other organic chemical suppliers) in 80% yield.

In the reaction of the bis(substituted-pentadienyl)ruthenium compound with the cyclopentadiene compound, the concentration of the bis(substituted-pentadienyl)ruthenium compound can vary over a wide range, and need only be that minimum amount necessary to react with the cyclopentadiene compound to give the high nucleation density organometallic ruthenium compounds of this invention. In general, depending on the size of the reaction mixture, bis(substituted-pentadienyl)ruthenium compound concentrations in the range of from about 1 millimole or less to about 1000 millimoles or greater, should be sufficient for most processes.

In the reaction of the bis(substituted-pentadienyl)ruthenium compound with the cyclopentadiene compound, the concentration of the cyclopentadiene compound can vary over a wide range, and need only be that minimum amount necessary to react with the bis(substituted-pentadienyl)ruthenium compound to give the high nucleation density organometallic ruthenium compounds of this invention. In general, depending on the size of the reaction mixture, cyclopentadiene compound concentrations in the range of from about 1 millimole or less to about 1000 millimoles or greater, should be sufficient for most processes.

The solvent employed in the processes of this invention may be any saturated and unsaturated hydrocarbons, aromatic hydrocarbons, aromatic heterocycles, alkyl halides, silylated hydrocarbons, ethers, polyethers, thioethers, esters, lactones, amides, amines, polyamines, nitriles, silicone oils, other aprotic solvents, or mixtures of one or more of the above; more preferably hexanes, pentanes, or dimethoxyethanes; and most preferably diethylether or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting material.

In the reaction of the bis(substituted-pentadienyl)ruthenium compound with the cyclopentadiene compound, reaction conditions such as temperature, pressure and contact time may also vary greatly and any suitable combination of such conditions may be employed herein. The reaction temperature may be the reflux temperature of any of the aforementioned solvents, and more preferably between about −40° C. to about 100° C., and most preferably between about −20° C. to about 80° C. Normally the reaction is carried out under ambient pressure and the contact time may vary from a matter of seconds or minutes to a few hours or greater. The reactants can be added to the reaction mixture or combined in any order. The molar ratio of Zn:Ru in the starting materials may vary from about 1.5 to about 100. The molar ratio of substituted cyclopentadiene to bis(substitutedpentadienyl)ruthenium can range from about 0.8 to about 1.0.

The temperature of the solution during the addition of the substituted cyclopentadiene to the bis(substitutedpentadienyl)ruthenium intermediate may range between −80° C. and the refluxing temperature of the solution. The temperatures of the solutions in between process steps, and the time required for each process step may vary widely. The incubation time prior to heating the solution may vary from 0 minutes to about 3 days. The temperature that the solution is heated to may vary from about −50° C. (in which case the reaction is cooled and not heated) to the refluxing temperature of the solution (it should be noted that the pressure of the nitrogen environment over the reaction may be increased to increase the refluxing temperature of the solution). The length of stirring during each step of the reaction in which "heating" is involved may vary from 0 minutes to about 3 days.

When a substituted cyclopentadienyl compound is employed in the reaction, the cyclopentadienyl (or substituted analog) delivery may occur by a non-deprotonated diene (e.g., cyclopentadiene), preferably a lithium, potassium, thallium, ammonium, calcium, or magnesium salt of the cyclopentadienyl compound. The addition may be as a solid or in the alternative, as a solution with any solvents listed above, preferably the sodium salt in ~1-2M solution.

The stir time employed in the processes of this invention can range from about 0.1 to about 200 hours for all steps, more preferably from about 2 to about 100 hours for bis (substituted-pentadienyl)ruthenium preparation, and from about 0.1 to about 48 hours for cyclopentadienyl addition. More preferably, the stir time can range from about 2 to 16 hours for bis(substituted-pentadienyl)ruthenium preparation, and 0.1 to 1 hour for cyclopentadienyl addition.

It is preferred that all of the reactions described above are carried out in nitrogen gas or a noble gas atmosphere. Examples of noble gases include helium, neon, argon, krypton, xenon and radon. Among these gases, nitrogen and argon are preferable since they are economically available.

Other alternative processes that may be used in preparing the high nucleation density organometallic ruthenium compounds of this invention include those disclosed in U.S. Pat. No. 6,605,735 B2 and U.S. patent application Ser. No. 10/685,777, filed Oct. 16, 2003, the disclosure of which is incorporated herein by reference.

The process of the invention may employ a 2,4-dimethylpentadienyl anion, such as generally found in the presence of a counterion in 2,4-dimethylpentadienide or other functionalized pentadienide-like salts (PD). Examples of suitable counterions include Na, Li, K. Mg, Ca, Tl cations or TMS. Specific examples of 2,4-dimethylpentadienide or pentadienide-like salts include but are not limited to Li(PD), K(PD) or Na(PD).

In an embodiment, the process of the invention involves combining a metal salt compound, a ligand (L") compound and a first disubstituted or polysubstituted cyclopentadiene compound (Cp), for instance 1,3-dimethylcyclopentadiene or indene (HCp), to form an intermediate compound; and reacting the intermediate compound with a pentadienide compound, e.g., including a pentadienyl, 2,4-dimethylpentadienyl or another functionalized pentadienyl anion, such as described above.

The metal salt can be a metal (III) salt, such as, for example, a metal halide (e.g., chloride, bromide, iodide, fluoride), a metal nitrate and other suitable metal salts. M" can be a Group 8 (VIII) metal, e.g., Ru, Os or Fe. Generally, the metal salt is abbreviated as M"$X_n$. As used herein, the abbreviation M"$X_n$ does not exclude metal salt compounds that include water of hydration and that, as known in the art, can be more specifically represented by the formula M"$X_n$.$\mu H_2O$, $\mu$ being other than 0. Thus in specific examples, the abbreviation $FeX_3$ used herein includes anhydrous as well as hydrated iron salts that can be employed to form ferrocenes or ferrocene-like compounds.

Ligand (L") generally is an electron pair donor compound. A neutral electron pair donor, such as, for example, triphenylphosphine ($PPh_3$) may be employed. Tricyclohexylphosphine and other phosphines of the general formula $PR_3$, as well as phosphite triesters, $P(OR)_3$, where R is phenyl, cyclohexyl, alkyl or branched alkyl, e.g., t-butyl, group, also can be employed. Other suitable electron pair donors include amines, phosphates, carbonyl compounds, olefins, polyolefins, chelating phosphines, chelating amines and others.

Preferably, the Cp compound is a disubstituted cyclopentadienyl compound, e.g., 1,3'-dimethylcyclopentadiene, or indene, and can be polysubstituted. The Cp compound also can be provided as a salt including a disubstituted cyclopentadienyl, polysubstituted cyclopentadienyl or indenyl anion. Suitable cations that can be used with the anion, include, but are not limited to, TMS, Na, Li, K. Mg, Ca and Tl. Specific examples of salts include KCp, NaCp or LiCp.

Each of the M"$X_n$, L" and Cp components can be provided in neat form or can optionally include a suitable solvent. Preferred solvents that can be employed in the process of the invention include alcohols, such as, for instance, ethanol, methanol, isopropanol and other alcohols. Ethyl acetate, tetrahydrofuran (THF), saturated or unsaturated hydrocarbons, aromatic heterocycles, alkyl halides, silylated hydrocarbons, ethers, polyethers thioethers, esters, lactones, amides, amines, polyamines, nitriles, silicone oils and other aprotic solvents also can be employed. Combinations of solvents also can be employed.

Generally, concentrations of M"$X_n$, L" and Cp are selected as known in the art. For example, the molar concentration of M"$X_n$ in a suitable solvent can be in the range of from about 0.1 M to neat. That of L" in a suitable solvent can be in the range of from about 0.1 M to neat. The molar concentration of Cp in a suitable solvent can be in the range of from about 0.1 to neat. If neat phosphine is employed, it is believed that the reaction would be highly exothermic. Methods and systems for dissipating substantial amounts of heat of reaction per unit volume are known in the art.

The three components can be combined in any order. In one embodiment, the metal component and the HCp component are added concurrently to the L' component. In another embodiment, the metal component and the HCp component are combined to form a mixture and then the mixture is combined with the L" component, for instance by adding the L" compount to the mixture. In yet another embodiment, all components are combined at the same time.

Typically the molar ratio of HCp to M"$X_n$ used is in the range from about 50 to about 1, preferably from about 12 to about 2 and most preferably in the range from about 7 to about 5. Typically, the molar ratio of L to M"$X_n$ is in the range of from about 8 to about 0, preferably from about 6 to about 2 and most preferably from about 5 to about 3.5.

The reaction temperature preferably is around the boiling point of the solvent employed or the boiling point of the reaction mixture. Other suitable temperatures can be determined by routine experimentation. Generally, the reaction can be conducted at a temperature that is in the range of from above the freezing point to about the boiling point of the reaction composition. For instance, the reaction can be conducted at a temperature in the range of from about −100° C. to about 150° C.

The time of reaction generally depends on temperature, and concentration of the various reactants, and can range, for example, from about 5 minutes to about 96 hours.

The intermediate compound formed by the reaction of the metal salt M"$X_n$, L" and Cp compound, e.g., HCp, can be represented by the formula CpM"L"$_f$X, where f=1 or 2.

In one embodiment, CpM"L"$_f$X is isolated, e.g., as a solid, by methods known in the art. Examples of techniques that can be employed to isolate the intermediate compound include filtration, centrifugation and recrystallization.

In another example, no isolation of an intermediate compound from the reaction solution is carried out.

Whether isolated or not, the intermediate compound is reacted with a pentadienide compound, preferably in the presence of a solvent.

The pentadienyl group preferably is provided as an anion in combination with a counterion, e.g., TMS, Na, Li, K, Mg, Ca, Tl. Specific examples of pentadienide, or pentadienide-like salts that can be employed to provide the pentadienyl moiety include K(PD), Li(PD), Na(PD) and others. The pentadienide can be as defined above.

In an embodiment of this invention, intermediate CpM"L"$_f$X is reacted with sodium or lithium 2,4-dimethylpentadienide. Anions of substituted or unsubstituted 1,3-dienes can also be used.

In an embodiment, the intermediate compound is (Me$_2$Cp)Ru(PPh$_3$)$_2$Cl. It is reacted with a salt of PD. Recommended salts of PD include Na(PD), Li(PD), (PD)$_2$Mg, TMS(PD) and (PD)Tl.

Examples of suitable solvents for conducting the reaction between CpM"L"$_f$X and the pentadienide component include benzene, toluene, xylenes, pentanes, hexanes, petroleum ether, aromatic heterocycles, saturated or unsaturated hydrocarbons, alkyl halides, silylated hydrocarbons, ethers, polyethers, thioethers, esters, lactones, amides, amines, polyamines, nitriles, silicones, and others.

Generally, the molar concentrations of the pentadienide component in a solvent can be in the range of from about 0.1 M to about 3.5 M, preferably in the range of from about 0.5 M to about 2.5 M and most preferably in the range of from about 1.4 to about 1.8 M.

Typically, the molar ratio of pentadienide relative to the CpM"L"$_f$X is in the range from about 50 to about 1, preferably from about 6 to about 1 and most preferably from about 1.6 to about 1.2.

The reaction between the pentadienide compound and the intermediate compound (whether isolated or not) is conducted at a temperature such as generally described above and results in the formation of CpM"(PD) product.

The product of the reaction, CpM"(PD), can be isolated and or purified by methods known in the art, such as, for example, solvent, e.g., hexane, extraction followed by distillation, sublimation or chromatography or directly by distillation, sublimation or chromatography. Recrystallization, ultracentrifugation and other techniques also can be employed. Alternatively, the product can be employed in the reaction mixture without further isolation and or purification.

The process of the invention also can be used to form osmium-based compounds and iron-based compounds. Similarly, the method of the invention can be used to form organometallic compounds including other $\eta$"-coordinated aromatic moieties.

The sequence of employing the Cp and PD compounds in the process of this invention is not narrowly critical. For example, this invention encompasses reaction sequences in which the M"$X_n$, L" and PD' components may be reacted to form an intermediate compound and the intermediate compound thereafter reacted with a Cp' compound to form the product Cp'M"(PD').

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organometallic ruthenium compounds formed by the synthetic methods described above include, but are not limited to, analytical gas chromatography, nucleation magnetic resonance, thermogravimetric analysis, inductively coupled plasma mass spectrometry, vapor pressure and viscosity measurements.

Relative vapor pressures, or relative volatility, of organometallic ruthenium compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

As indicated above, this invention relates in part to a method for producing a film, coating or powder. The method includes the step of decomposing at least one organometallic ruthenium compound precursor, thereby producing the film, coating or powder, as further described below. Suitable substrates include those comprised of a material selected from the group consisting of a metal, a metal silicide, a semiconductor, an insulator and a barrier material (e.g., for disruptive barrier applications).

Organometallic ruthenium compound precursors described herein are well suited for preparing in-situ powders and coatings. For instance, a liquid organometallic ruthenium compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic ruthenium compound precursor, and heating and decomposing it, thereby forming a first layer, followed by at least one other coating with the same or a different precursors, and heating.

Liquid organometallic ruthenium compound precursors such as described above also can be atomized and sprayed onto a substrate. Atomization and spraying means, such as nozzles, nebulizers and others, that can be employed are known in the art.

In preferred embodiments of the invention, an organometallic ruthenium compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic ruthenium compound precursor, such as described above, also can be employed in a given process.

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic ruthenium compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

Deposition processes described herein can be conducted to form a film, powder or coating that includes a single metal, e.g, a Ru-film, or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic ruthenium compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of ruthenium, for instance, can be considered for fabricating metal electrodes, in particular as p-channel metal electrodes in logic, and as capacitor electrodes for DRAM applications.

The process also is suited for preparing layered films, wherein at least two of the layers differ in phase or composition. Examples of layered film include metal-insulator-semiconductor, and metal-insulator-metal.

In an embodiment, the invention is directed to a process that includes the step of decomposing vapor of an organometallic ruthenium compound precursor described above, thermally, chemically, photochemically or by plasma activation, thereby forming a film on a substrate. For instance, vapor generated by the compound, a liquid at room temperature, is contacted with a substrate having a temperature sufficient to cause the organometallic ruthenium compound to decompose and form a film on the substrate.

The organometallic ruthenium compound precursors can be employed in chemical vapor deposition or, more specifically, in metalorganic chemical vapor deposition processes known in the art. For instance, the organometallic ruthenium compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic ruthenium compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The process of the invention can be conducted in various chemical vapor deposition reactors, such as, for instance, hot or cold-wall reactors, plasma-assisted, beam-assisted or laser-assisted reactors, as known in the art.

Precursors that are liquid at room temperature are preferred during chemical vapor deposition manufacturing and the organometallic ruthenium compounds of this invention have properties that make them suitable as chemical vapor deposition precursors.

Examples of substrates that can be coated employing the process of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The process of the invention can be conducted to deposit a film on substrate that has a smooth, flat surface. In an embodiment, the process is conducted to deposit a film on a substrate used in wafer manufacturing or processing. For instance, the process can be conducted to deposit a film on patterned substrates that include features such as trenches, holes or vias. Furthermore, the process of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometer thick. Films that are less than 50 nanometer thick, for instance, films that have a thickness between about 20 and about 30 nanometer, also can be produced.

Organometallic ruthenium compound precursors described above also can be employed in the process of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. millimeters) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The process of the invention also can be conducted using supercritical fluids. Examples of film deposition methods that use supercritical fluid that are currently known in the art include chemical fluid deposition, supercritical fluid transport-chemical deposition, supercritical fluid chemical deposition, and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic ruthenium compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic ruthenium compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above an organometallic ruthenium compound precursor can be used alone or in combination with one or more components, such as, for example, other organometallic precursors, inert carrier gases or reactive gases.

In a system that can be used in producing films by the process of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic ruthenium compound precursors described above can be employed to produce films that include a single metal, e.g, a Ru-film, or a film that includes a single metal oxide. Mixed films also can be deposited, for instance mixed metal oxide films. Such films are produced, for example, by employing several organometallic precursors, at least one of which being selected from the organometallic ruthenium compounds described above. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

Synthesis of (1,3-dimethylcyclopentadienyl)(2,4-dimethylpentadienyl)ruthenium

A dry 1 liter 3-neck round-bottom flask was charged with a magnetic stir bar and equipped with three septa. A nitrogen purge was introduced through a needle with output, also via a needle, to an oil bubbler. A thermocouple lead was placed through a side neck septa. Excess zinc (150 grams, 'dust' was found more conducive to stirring) was added to the flask. By syringe, 2,4-dimethyl-1,3-pentadiene (25 grams, 0.26 mol) was added to the flask. By cannula, ruthenium trichloride hydrate (6.0 grams, 0.023 mol based on 3 hydrate equivalents) was added as a methanol (250 milliliters) solution in spurts of about 10 milliliters over 45 minutes. The mixture was stirred for 30 minutes at 25° C. after the addition was complete, then, upon equipping a condenser, the contents were brought to gentle reflux. Stirring was continued for 2 hours. The mixture was cooled to 25° C., followed by the addition of freshly distilled 1,3-dimethylcyclopentadiene (2.2 grams, 0.023 mol) by syringe over 20 minutes. Stirring was continued at 25° C. for 20 additional minutes, followed by gentle reflux for 2 hours.

Upon cooling, the reaction was filtered through Celite yielding a dark brown solution. The product was extracted with hexanes. The hexanes were removed to yield a dull-yellow solid (3.8 grams, 0.013 mol, 57% yield). This product (97% pure by GC-MS) may be purified to >99.5% (GC-MS) by chromatography (alumina/hexanes). Mass spectrum, m/e (relative intensity): 287 (100), 288 (91), 290 (99). 1H NMR (300 MHz, toluene-d8, d): 5.06 (s, 1H), 4.34 (br t, 1H,), 4.23 (d, 2H, J=1 Hz)), 2.46 (dd, 2H, J=1,3 Hz), 1.76 (s, 6H), 1.60 (s, 6H), 0.22 (dd, 2H, J=1,3 Hz).

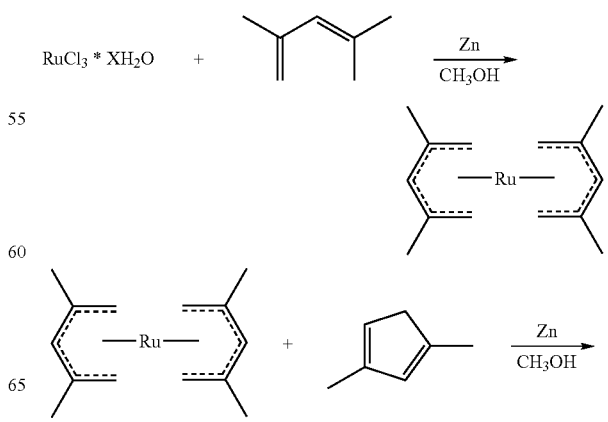

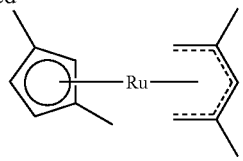

EXAMPLE 2

Synthesis of (1,3-dimethylcyclopentadienyl)(2,4-dimethylpentadienyl)ruthenium

A 2 liter three-necked round bottomed flask is charged with a Teflon7 stirring bar, ethanol (1.0 liter) and PPh3 (263 grams, 1.0 mol). A 250 milliliter dropping funnel, a 150 milliliter bath-jacketed dropping funnel, and a condenser are attached to the three necks of the 2 liter flask. It is important to note that both dropping funnels are equipped with Teflon7 valves that permit their isolation from the atmosphere of the round-bottomed flask. A rubber septum is connected to the top of the 150 milliliter bath-jacketed dropping funnel. The top of the condenser is fitted with a T junction adapter and connected to an inert atmosphere. A heating mantle is placed beneath the 2 liter, three-necked round-bottomed flask and the solution is stirred and heated to reflux. At reflux, all of the triphenylphosphine dissolves in the ethanol. The system is purged with nitrogen for 3 hours while at reflux.

While this is taking place, a 500 milliliter erlenmyer flask is charged with $RuCl_3 \cdot XH_2O$ (50 grams, 0.20 mol), ethanol (150 milliliters) and a Teflon7 coated magnetic stirring bar. The ethanolic solution immediately develops a brown/orange color. To dissolve all of the $RuCl_3 \cdot XH_2O$, it is necessary to slowly heat the solution. This solution is poured into the 250 milliliter dropping funnel. The solution is sparged with nitrogen for 30 minutes by inserting a needle connected to a 1-2 pounds per square inch gauge (psig) nitrogen source through the septum and into the solution and by piercing the septum with another needle to allow for relief of excess pressure.

A methanol/dry ice bath is made up in the 150 milliliter bath-jacketed dropping funnel. The interior of this dropping funnel is purged with nitrogen for 30 minutes in a similar fashion to which the other dropping funnel was sparged. 2,4-dimethyl-1,3-pentadiene (116 grams, 1.2 mol, freshly distilled under a nitrogen atmosphere) is then cannulated into the cooled dropping funnel through the rubber septum.

After 3 hours of purging the 2 liter, round bottomed flask has elapsed, the Teflon7 valves isolating the dropping funnels from the rest of the system are both opened and dropwise addition of the two solutions commences simultaneously. Over the course of 20 minutes the two solutions are both added to the ethanolic PPh3 solution. During this entire time the solution is at reflux. The solution quickly develops a deep orange brown color.

After the addition is completed, the solution is left to reflux for an additional 2 hours. During this time small orange red crystals can be seen accumulating above the meniscus of the solution on the walls of the 2 liter flask.

The solution is allowed to cool to slightly below reflux and the contents of the 2 liter flask are filtered (open to air) over a coarse frit. The red/orange solid is collected (anticipated yield of 195 grams). The filtrate is discarded and the solid is placed in a vacuum oven at 60° C. overnight.

The solid is removed from the vacuum oven and tared on an analytical balance (anticipated to be approximately 150 grams). Based on this, the yield of crude chloro(2,4-dimethylpentadienyl)bis(triphenylphosphine)ruthenium(II) is determined.

Next, in a nitrogen glovebox, a 1 liter flask is charged with toluene (500 mL, anhydrous), the crude chloro(2,4-dimethylpentadienyl)bis(triphenylphosphine)ruthenium(II) (150 grams, 0.20 mol) and a Teflon7 stir bar. The solution is stirred and sodium 1,3-dimethylcyclopentadienide (41 grams, 0.35 mol) is slowly added over the course of one hour. Following this addition, the solution is stirred for 4 hours at 80° C. At this stage the flask was removed from the glovebox and the majority of toluene was removed using a rotary evaporator. Hexanes (500 milliliters) is then added to the flask and the contents are stirred for 30 minutes. This solution is then filtered through a plug of silica over a coarse frit. A brown/red solid is separated from the yellow/orange filtrate. The filtrate is then placed in a freezer and crystalline solid (PPh3) precipitates from the solution. The liquid is decanted from the solid and the solution is again concentrated using a rotary evaporator. This solution is left overnight and crystals (PPh3) are evident in the flask the following morning. The liquid is decanted into a 100 milliliter round-bottomed flask.

The 100 milliliter round-bottomed flask is fitted with a short path distillation adapter with vigreux indentations and a 100 milliliter storage flask receptacle. The liquid is distilled under vacuum and a clear yellow liquid, (2,4-dimethylpentadienyl)(1,3-dimethylcyclopentadienyl)ruthenium containing 1-3% triphenylphosphine is obtained. Spinning band distillation of the yellow liquid affords 47.6 grams (83% yield) of triphenylphosphine free (2,4-dimethylpentadienyl)(1,3-dimethylcyclopentadienyl)ruthenium at >99.7+% purity (GCMS)

The invention claimed is:

1. A high nucleation density organometallic compound represented by the formula LML' wherein M is a transition metal, L is a substituted cyclopentadienyl-like group, and L' is unsubstituted pentadienyl-like group, wherein the substituted cyclopentadienyl-like group is selected from cyclohexadienyl, cycloheptadienyl, cyclooctadienyl, heterocyclic group and aromatic group, and the substituted or unsubstituted pentadienyl-like group is selected from linear olefins, hexadienyl, heptadienyl and octadienyl.

2. A high nucleation density organometallic compound represented by the formula $(L)_2M'L'$ or $LM'(L')_2$ wherein M' is lanthanide, L is the same or different and is a substituted cyclopentadienyl group or substituted cyclopentadienyl-like group, and L' is the same or different and is a substituted or unsubstituted pentadienyl group or a substituted or unsubstituted pentadienyl-like group.

3. The high nucleation density organometallic compound of claim 1 represented by the formula LRuL'.

4. A process for producing a high nucleation density organometallic ruthenium compound which comprises reacting a bis(substituted-pentadienyl)ruthenium compound represented by the formula

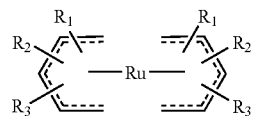

with a substituted cyclopentadiene compound represented by the formula

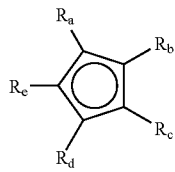

wherein $R_a$ and $R_c$ are the same or different and each represents a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, and $R_b$, $R_d$, $R_e$, $R_1$, $R_2$, and $R_3$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms or an alkyl group having from 1 to about 12 carbon atoms, under reaction conditions sufficient to produce said high nucleation density organometallic ruthenium compound.

5. The process of claim 4 wherein the bis(substituted-pentadienyl)ruthenium compound is represented by the formula

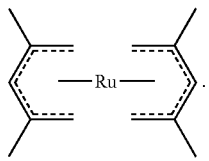

6. The process of claim 4 wherein the substituted cyclopentadiene compound is represented by the formula

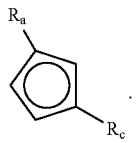

7. A process for producing a high nucleation organometallic compound which comprises reacting a metal salt ($M''X_n$) compound, a cyclopentadienyl compound (Cp) and a ligand (L") under reaction conditions sufficient to form an intermediate compound; and reacting the intermediate compound with a pentadienide compound (PD) under reaction conditions sufficient to produce the high nucleation organometallic compound, wherein M" is a Group VIII metal, L" is an electron pair donor compound, Cp is a disubstituted or polysubstituted cyclopentadienyl compound, and PD is a pentadienide-like salt.

8. A process for producing a high nucleation organometallic compound which comprises reacting a metal salt ($M''X_n$) compound, a pentadienyl compound (PD') and a ligand (L"') under reaction conditions sufficient to form an intermediate compound; and reacting the intermediate compound with a cyclopentadienide compound (Cp') under reaction conditions sufficient to produce the high nucleation organometallic compound, wherein M" is a Group VIII metal, L" is an electron pair donor compound, PD' is a pentadienyl compound, and Cp' is a disubstituted or polysubstituted cyclopentadienide-like salt.

9. A method for producing a film, coating or powder by decomposing a high nucleation density organometallic compound precursor represented by the formula LML' wherein M is a transition metal, L is a substituted cyclopentadienyllike group, and L' is a substituted or unsubstituted pentadienyl-like group, wherein the substituted cyclopentadienyl-like group is selected from cyclohexadienyl, cycloheptadienyl, cyclooctadienyl, heterocyclic group and aromatic group, and the substituted or unsubstituted pentadienyl-like group is selected from linear olefins, hexadienyl, heptadienyl and octadienyl, thereby producing the film, coating or powder.

10. The method of claim 9 wherein the decomposing of said high nucleation density organometallic compound precursor is thermal, chemical, photochemical or plasma-activated.

11. The method of claim 9 wherein said high nucleation density organometallic compound precursor is vaporized and the vapor is directed into a deposition reactor housing a substrate.

12. The method of claim 11 wherein the substrate is comprised of a material selected from the group consisting of a metal, a metal suicide, a semiconductor, an insulator and a barrier material.

13. The method of claim 11 wherein the substrate is a patterned wafer.

14. The method of claim 9 wherein the film, coating or powder is produced by a gas phase deposition.

15. A method for producing a film, coating or powder by decomposing a high nucleation density organometallic compound precursor represented by the formula $(L)_2M'L'$ or $LM'(L')_2$ wherein M' is a lanthanide, L is the same or different and is a substituted cyclopentadienyl group or substituted cyclopentadienyl-like group, and L' is the same or different and is a substituted or unsubstituted pentadienyl group or a substituted or unsubstituted pentadienyl-like group, thereby producing the film, coating or powder.

16. The method of claim 15 wherein the decomposing of said high nucleation density organometallic compound precursor is thermal, chemical, photochemical or plasma-activated.

17. The method of claim 15 wherein said high nucleation density organometallic compound precursor is vaporized and the vapor is directed into a deposition reactor housing a substrate.

18. The method of claim 17 wherein the substrate is comprised of a material selected from the group consisting of a metal, a metal suicide, a semiconductor, an insulator and a barrier material.

19. The method of claim 17 wherein the substrate is a patterned wafer.

20. The method of claim 15 wherein the film, coating or powder is produced by a gas phase deposition.

* * * * *